(12) United States Patent
Valerino, Sr. et al.

(10) Patent No.: US 6,712,561 B1
(45) Date of Patent: Mar. 30, 2004

(54) DISPOSAL OF SHARPS IN A HEALTHCARE ENVIRONMENT

(76) Inventors: Frederick M. Valerino, Sr., 327 Gailridge Rd., Timonium, MD (US) 21093; Frederick M. Valerino, Jr., 19508 Cameron Mill Rd., Parkton, MD (US) 21120

( * ) Notice: Subject to any disclaimer, the term of this patent is extended or adjusted under 35 U.S.C. 154(b) by 0 days.

(21) Appl. No.: 10/252,893

(22) Filed: Sep. 23, 2002

(51) Int. Cl.⁷ ............................................. B65G 53/00
(52) U.S. Cl. ......................... 406/197; 406/19; 406/31; 406/117; 406/147
(58) Field of Search ........................... 406/19, 31, 117, 406/147, 197

(56) References Cited

U.S. PATENT DOCUMENTS

| | | | | |
|---|---|---|---|---|
| 3,759,577 A | * | 9/1973 | Manzer | 406/117 |
| 3,953,078 A | * | 4/1976 | Aitken | 406/117 |
| 4,076,321 A | * | 2/1978 | Haight et al. | 406/117 |
| 4,108,498 A | * | 8/1978 | Bentsen | 406/117 |
| 4,157,796 A | * | 6/1979 | Warmann | 406/31 |
| 4,210,801 A | * | 7/1980 | Gomez et al. | 377/7 |
| 4,995,765 A | | 2/1991 | Tokuhiro et al. | 406/117 |
| 5,234,292 A | | 8/1993 | Lang | 406/1 |
| 5,385,105 A | | 1/1995 | Withers, Jr. et al. | 110/346 |
| 6,283,909 B1 | | 9/2001 | Sharp | 588/258 |

* cited by examiner

*Primary Examiner*—Joseph A. Dillon

(57) ABSTRACT

A method of disposing of hazardous materials wherein a dedicated pneumatic tube system is used. The pneumatic tube system has a plurality of loading stations all connected to a single destination station. The hazardous materials are placed in a disposable carrier which is transported to the destination station. Each disposable carrier has a marker which identifies the disposable carrier. A control unit cooperates with the markers and activates the pneumatic tube system. The disposable carrier is a cylinder with a sealable cover.

8 Claims, 8 Drawing Sheets

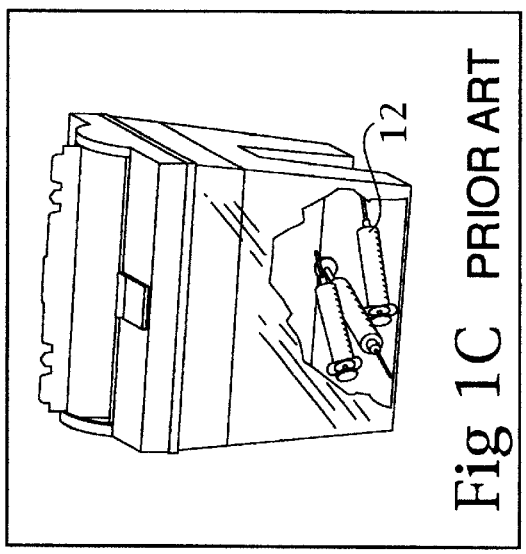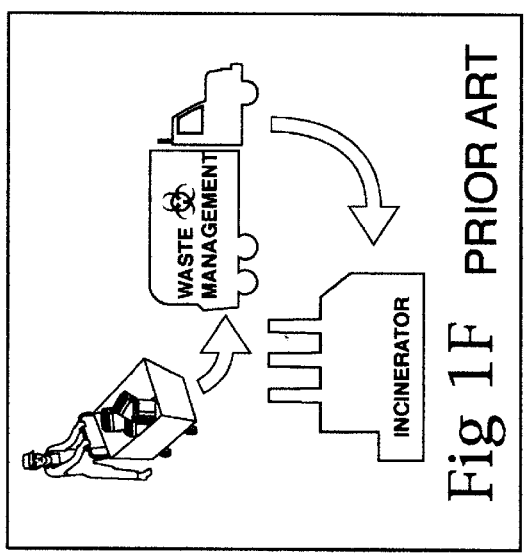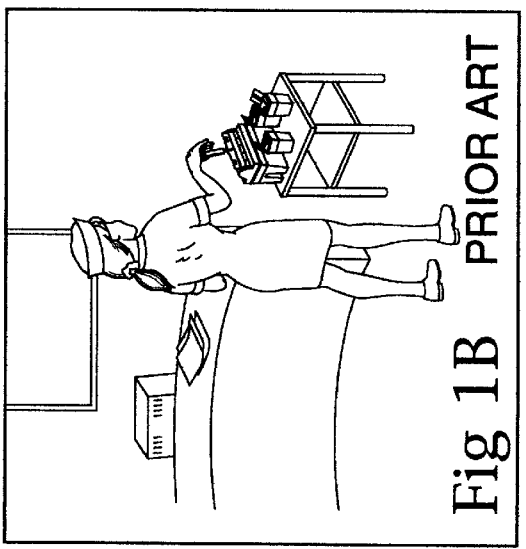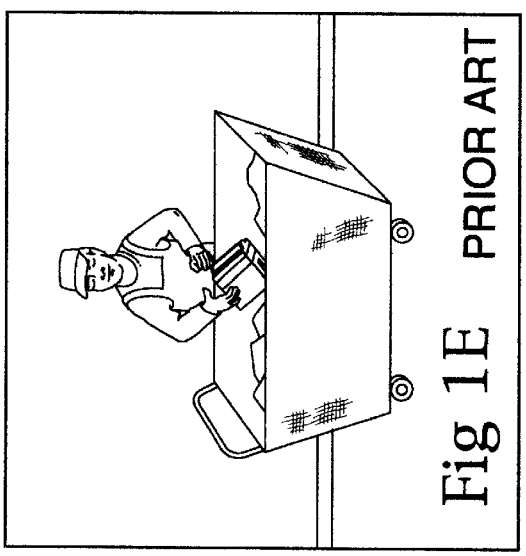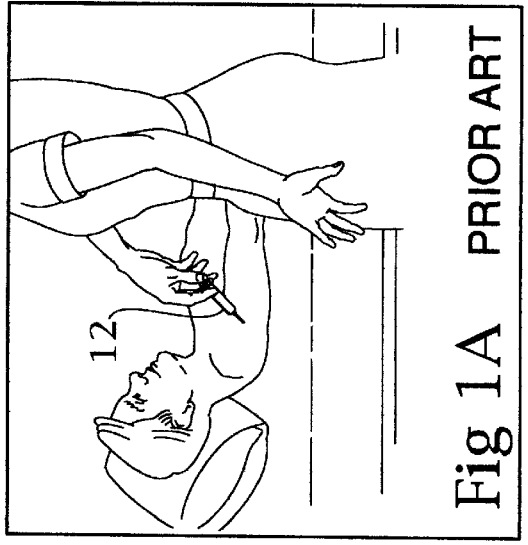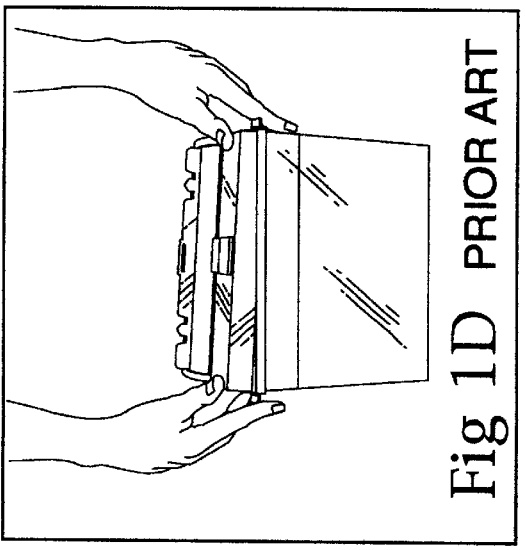

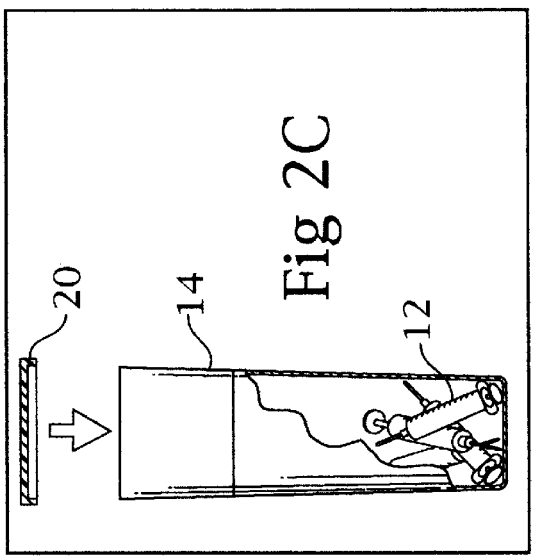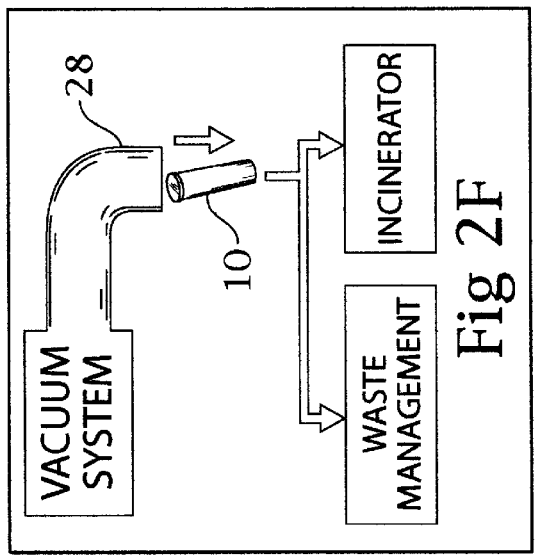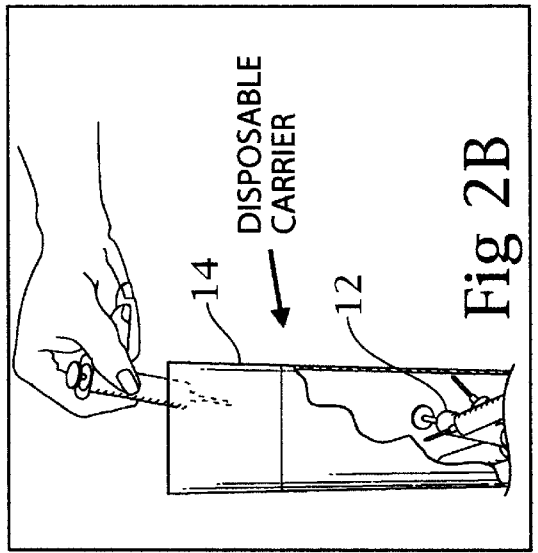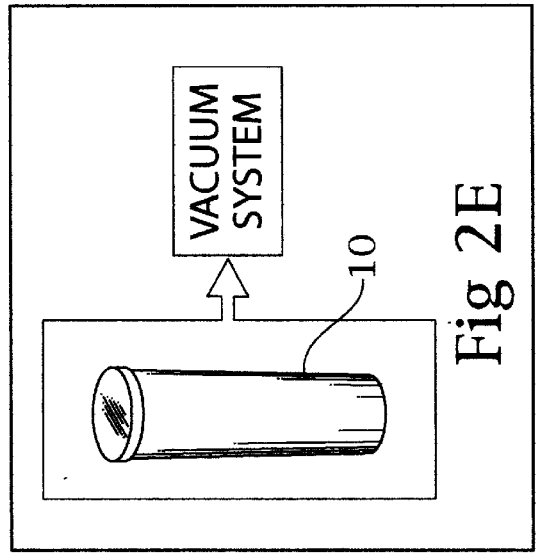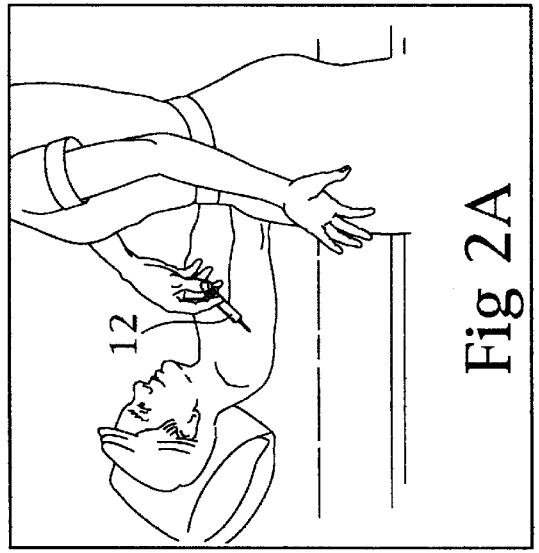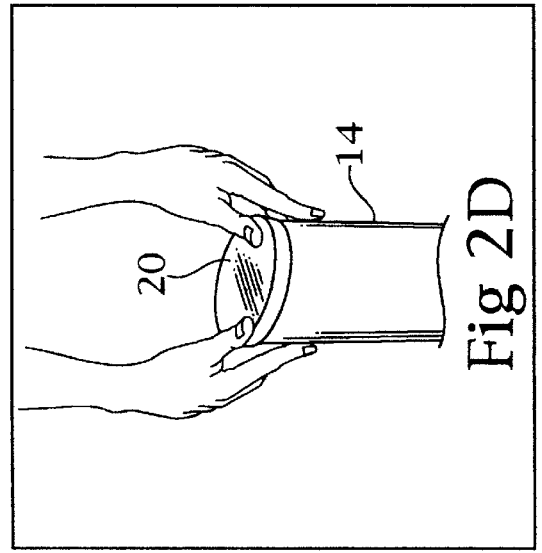

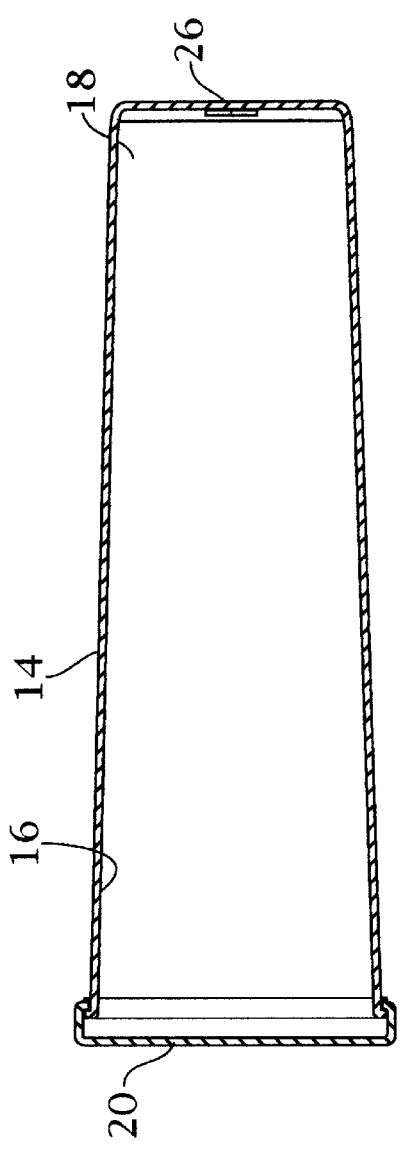
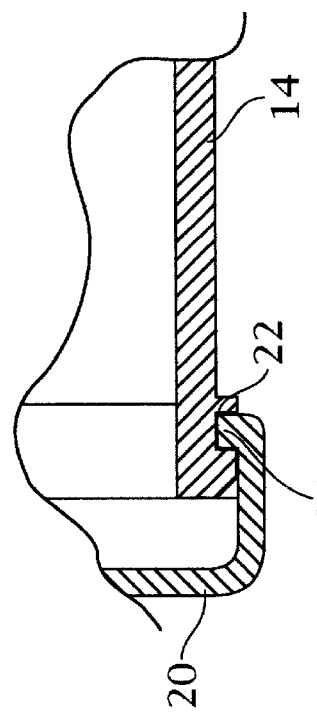
Fig 4
Fig 5
Fig 3

DISPOSAL OF SHARPS IN A HEALTHCARE ENVIRONMENT

BACKGROUND OF THE INVENTION

1. Field of the Invention

The present invention relates to the safe disposal of "sharps" in a healthcare, hospital or clinical environment and more particularly, to a disposable carrier for containing the "sharps" and to be transported in a pneumatic tube system.

2. Description of the Related Art

Pneumatic tube systems, per se, are quite old. They have been used in department stores, banks and many other installations. The use of these systems in department stores and banks is primarily for movement of currency, deposit slips, sales slips and related commercial transactions. The pneumatic tubes are for two-way traffic between the stations. In a bank, the tubes may be between a drive-in station and a teller in the bank. In a department store, the tubes may be between several different departments and a cashier or accounting office. The pneumatic tube systems used in hospitals are not single use but, rather, are "global" usually having a keypad or its equivalent so that the sender can select the destination of the carrier, such as the cashier, pharmacy, pathology lab, etc. Moreover, the carrier (receptacle or container) does not carry any biohazardous or hazardous product, such as "sharps". Examples of "sharps" are a used scalpel blade, needle or syringe. Hence, the carrier is reusable and not permanently sealed.

Disposal of "sharps" is a pressing problem for the medical community because of the enormous volume of these potentially fatal items. Present practice is for the "sharps" to be placed in containers which are strategically located throughout a hospital or clinical environment. These could be emergency rooms, operating rooms, intensive care units, phlebotomy units, nurses stations and any other location where needles and/or scalpels may be used Typically, the containers have a non-removable lid which has a one-way opening into which the "sharps" are introduced. When the container has been filled to a premarked level, the container is placed at a central point such as a nurses station in the hospital. A plurality of filled containers accumulate and are collected on a periodic basis for disposal as hazardous waste. The filled containers are subject to removal by unauthorized persons and could be a source of serious infections.

The applicant is aware of the following U.S. patents related to pneumatic tube systems and "sharps" disposal.:

Tokuhiro et al U.S. Pat. No. (4,995,765) teach a sanitary waste collection system and method for disposal. A hospital is disclosed as being a site at which the waste collection system is to be used. Tubes are used in the collection system. Substances can be conveyed in the tube by supplying air or vacuum to the tube. A rather sophisticated computer system is disclosed.

Lang U.S. Pat. No. (5,234,292) shows a pneumatic tube conveyor system. The conveyor system can be used in hospitals for distributing small-size articles such as medicines.

Withers et al U.S. Pat. No. (5,385,105) teach a "sharps" disposal container of a small cylindrical size. Withers et al does not disclose use with a pneumatic tube.

Sharp U.S. Pat. No. (6,283,909) teaches a "sharps" disposal container. This reference is cited only as background material. No pneumatic system is taught by the reference.

The more efficient and rapid way of delivering "sharps" to disposal area would be, obviously, by means of pneumatic tube system. Unfortunately, transporting "sharps" through existing (conventional) pneumatic tube system is unpractical because (a) sending "sharps" in standard multipurpose-multi-use carrier does not eliminate a possibility of injury, when a nurse or any other operator would open the carrier; (b) sending "sharps" in special single-use disposable carrier along with regular carriers inevitably would bring confusion and mistakes such as attempts to send things other than "sharps" in a single-use container, attempts to dispose the contents of a standard carrier in a waste bin, attempts to open the single-use carrier and so on.

There is a need for a dedicated single purpose pneumatic tube system in a healthcare, hospital or similar environment which has a disposable carrier dedicated to carrying potentially biohazardous or hazardous "sharps" from multiple sources to a single destination.

BRIEF SUMMARY OF THE INVENTION

It is an object of the present invention to provide a method having a dedicated pneumatic tube system for transport of hazardous material in a disposable carrier from multiple sending points to a single destination.

It is a further object of the present invention to reduce the possibility of injuries and contraction of disease due to exposure to "sharps".

It is another object of the present invention to provide a rapid, dedicated, safe pneumatic tube system from areas within a healthcare framework to a safe disposal area without manual personnel intervention.

It is still a further object of the present invention to provide a disposable carrier for hazardous materials which may be used in a pneumatic tube system.

In accordance with the teachings of the present invention, there is disclosed the method of disposing of biohazardous and/or hazardous "sharps" in a healthcare, hospital or clinical environment. A dedicated single-purpose pneumatic tube system and a disposable carrier are provided. A used "sharp" is inserted into the disposable carrier. The disposable carrier is closed so that the disposable carrier is sealed. The sealed disposable carrier, with the used "sharp" therein, is inserted into the dedicated single-purpose pneumatic tube system, such that the system recognizes the disposable carrier and is activated to move the disposable carrier through the system for ultimate disposal and/or destruction of the disposable carrier, and such that any other type of carrier will not activate the system.

In further accordance with the teachings of the present invention, there is disclosed a method of disposing of biohazardous and/or hazardous "sharps" in a healthcare, hospital or clinical environment. A dedicated single-purpose pneumatic tube system is provided having a plurality of loading stations and a single destination station. A plurality of disposable carriers are provided, each carrier having an identification means. A pneumatic tube system control unit is provided activated by the identification means on each of the disposable carriers. An operator inserts "sharps" in a selected one of the disposable carriers, seals said disposable carrier and introduces said disposable carrier into the pneumatic tube system at any loading station. The pneumatic tube system transports the disposable carrier containing the sharps to the destination station without any operator action.

Additionally, in accordance with the teachings of the present invention there is disclosed the method of disposing of biohazardous and/or hazardous "sharps" in a healthcare, hospital or clinical environment. A dedicated single-purpose pneumatic tube system is provided having a plurality of loading stations and a single destination station. A plurality of disposable carriers are provided, each carrier having an individual identification code. A pneumatic tube system control unit is provided. A code control unit is provided electronically connected to the pneumatic tube system. Sharps are inserted in the disposable carrier. The disposable carrier containing the sharps is placed in one of the loading stations. The code control unit recognizes the individual identification code on each disposable carrier and the code control unit activates the pneumatic tube system. The pneumatic tube system transports the disposable carrier containing the sharps to the destination station without any operator action.

In still further accordance with the teachings of the present invention, there is disclosed a disposable carrier to be used in combination with a pneumatic tube system having a plurality of loading stations and a single destination station in a hospital or clinical environment. The disposable carrier has a cylindrical container having an open top end and an opposite closed bottom end. A cover is sealably received on the open top end of the cylindrical container to retain contents of the cylindrical container therein. A marker is formed on the cylindrical container, the marker having therein coded information to identify the disposable carrier and to activate a sensor in the pneumatic tube system. Biohazardous and/or hazardous material is received in the disposable carrier and transported through the pneumatic tube system from any one of the plurality of loading stations to the destination station.

These and other objects of the present invention will become apparent from a reading of the following specification taken in conjunction with the enclosed drawings.

BRIEF DESCRIPTION OF THE DRAWINGS

FIG. 1A is a diagram showing a nurse administering medication to a patient using a hypodermic syringe and needle.

FIG. 1B is a diagram of the nurse depositing the needle in a sharps container of the prior art.

FIG. 1C is a partial cutaway view of the sharps container of the prior art showing sharps within the container.

FIG. 1D is a diagram of the nurse closing the lid on the sharps container of the prior art.

FIG. 1E is a diagram showing a waste disposal employee collecting the accumulated sharps containers of the prior art from the nurses station.

FIG. 1F is a diagram of disposal of a plurality of sharps containers of the prior art.

FIG. 2A is a diagram showing a nurse administering medication to a patient using a hypodermic syringe and needle.

FIG. 2B is a partial cross-sectional view showing the nurse putting the hypodermic syringe and the needle into the container of the present invention.

FIG. 2C is a partial cutaway view of the container of the present invention having sharps therein and a cover to be received on the container.

FIG. 2D is a diagram showing the cover being closed on the container.

FIG. 2E is a diagram showing the closed container inserted into the vacuum system.

FIG. 2F is a diagram showing the closed container leaving the vacuum system for disposal.

FIG. 3 is a top view of the disposable carrier.

FIG. 4 is a cross-sectional view taken along the lines 4—4 of FIG. 3.

FIG. 5 is an enlarged cross-sectional view of the lid received on the container.

DESCRIPTION OF THE PREFERRED EMBODIMENTS

Figure 6:
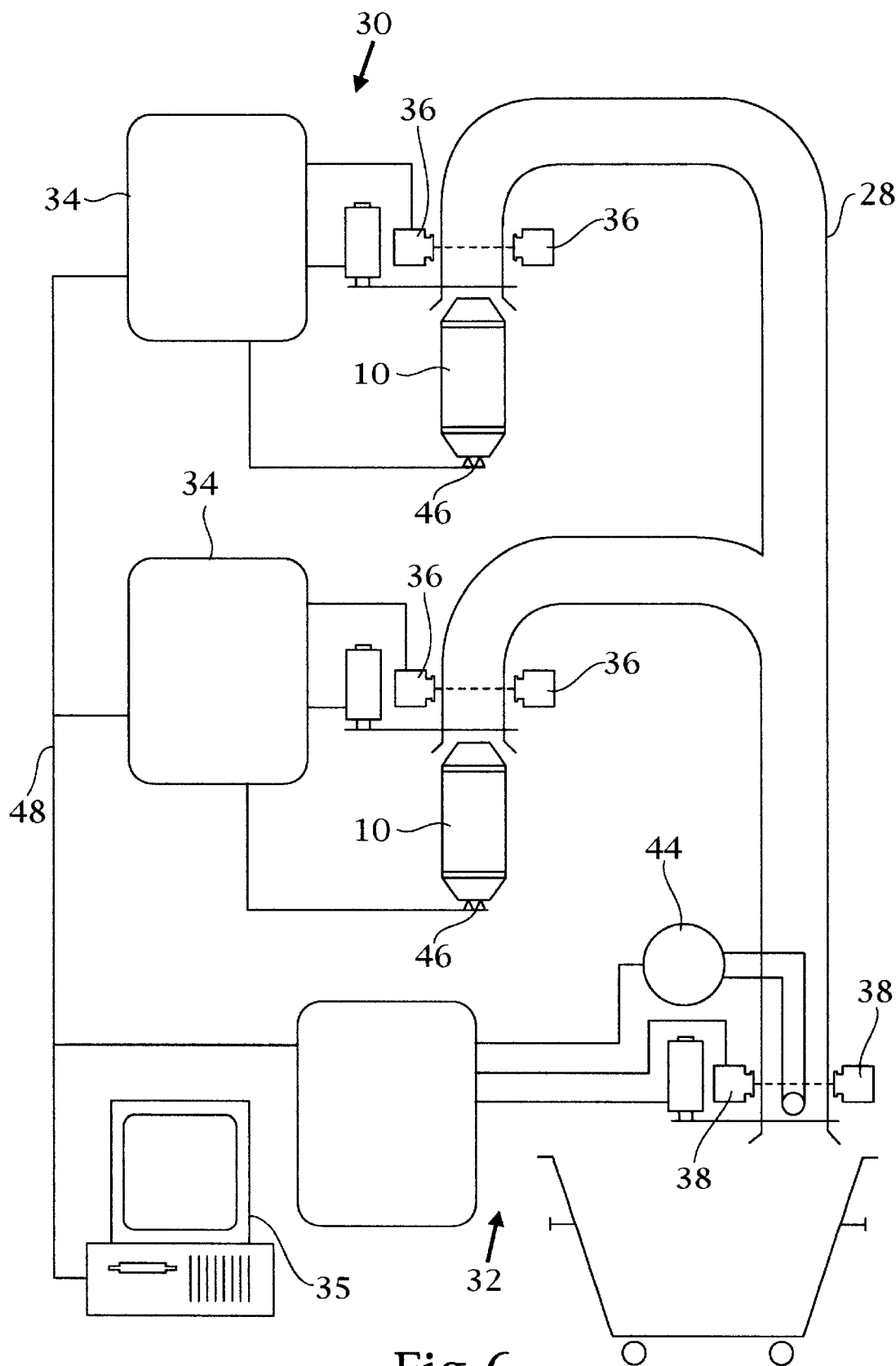
FIG. 6 is a schematic view showing two loading stations and one destination station of the overall system with control unit.

A disposable carrier 10 for "sharps" 12 is, preferably, a substantially cylindrical container 14 having an open top end 16 and a closed opposite bottom or second end 18. The container 14 may be tapered such that the top end 16 has a slightly greater diameter than the second end 18. Preferably, the container 14 is formed from a semi-flexible or flexible material which is resistant to punctures. A cover 20 is received on the open top end 16 of the cylindrical container 14 to retain contents within the container 14.

Preferably, the cylindrical container 14 has an annular groove 22 formed therein adjacent to the open top. The cover 20 has an annular lip 24 formed thereon. The top end 16 of the container 14 and/or the cover 20 may be flexed so that the lip 24 is cooperatively received in the groove 22 and the cover 20 is attached to the container 14. Alternately, the groove may be formed in the cover 20 and the lip 24 formed in the container 14. The cover 20 preferably forms a leak-proof seal with the container 14.

A marker 26 is attached to the cylindrical container 14. The marker 26 has therein coded information to identify the individual disposable carrier 10 and to activate a sensor as will be described. Preferably, each disposable carrier 10 has a unique identification to distinguish the disposable carrier from all other disposable carriers. The marker may be an electronics chip, a bar code, a foil, a magnetic strip or other markers known to persons skilled in the art. It is preferred that the marker be located on the bottom 18 of the container 14.

A dedicated single-purpose pneumatic tube system 28 is installed in the healthcare, hospital or clinical environment. The tube system may be either a positive pressure or a negative pressure (vacuum) system to move carriers through the tubes. The system consists of a plurality of loading stations 30 and a single destination station 32. In this manner, the disposable carriers 10 containing the "sharps" may be introduced into the tube system 28 from any of the loading stations 30. The loading stations 30 are most efficiently located where it is probable that the majority of the sharps will be generated. These stations include the operating rooms, the emergency rooms, the nurses stations, the intensive care unit and the phlebotomy unit. This system is not limited to the named locations. The dedicated tube system is so constructed that all of the loading stations 30 are directly connected to only the destination stations 32. Nothing can be inter-transmitted between any of the loading stations 30. At the destination station 32, waste management personnel collect the disposable carriers 10 and prepare the disposable carriers 10 which contain "sharps" for disposal. The disposable carriers 10 are not opened at the destination station 32. If an incinerator is available at the destination station 32, the disposable carrier 10 containing these sharps may be delivered directly into the incinerator. The maximum inner diameter of the tubes in the tube system is less than four inches to guarantee that the dedicated tube system 28 cannot be used with any reusable carrier. The reusable carriers on the market at the present time all have a minimum outer diameter of four inches or more.

Each disposable carrier 10 has a length of approximately nine inches. This length permits the disposable carrier to travel through the tube system which has bends and curves formed at a radius which do not hinder the movement of carriers with the prescribed length.

Because this single-purpose pneumatic tube system would coexist with a conventional pneumatic tube system in a hospital, it is extremely important to prevent any possibility of sending a disposable carrier with "sharps" through conventional system and vise versa of sending a heavy-loaded regular carrier through the single-purpose system.

Accordingly, in the present invention this goal is achieved by the combination of three features. First, this single-purpose pneumatic system employs the tubes with a gage not compatible with that of existing conventional systems. Second, the size (length) and shape of a disposable carrier 10 are different from multi-purpose multi-use carriers. Third, a disposable carrier 10 is supplied with a special marker bearing coded information and each loading station 30 of the system is supplied with a device (reader) 36 that reads this information when a carrier is inserted into a station for sending. The coded information may define an individual carrier (i.e., each carrier has its own unique number) or define the carrier as a member of a class (i.e., only carriers with the coded marker are accepted to by the system, but they could not be traced individually).

Figure 7:
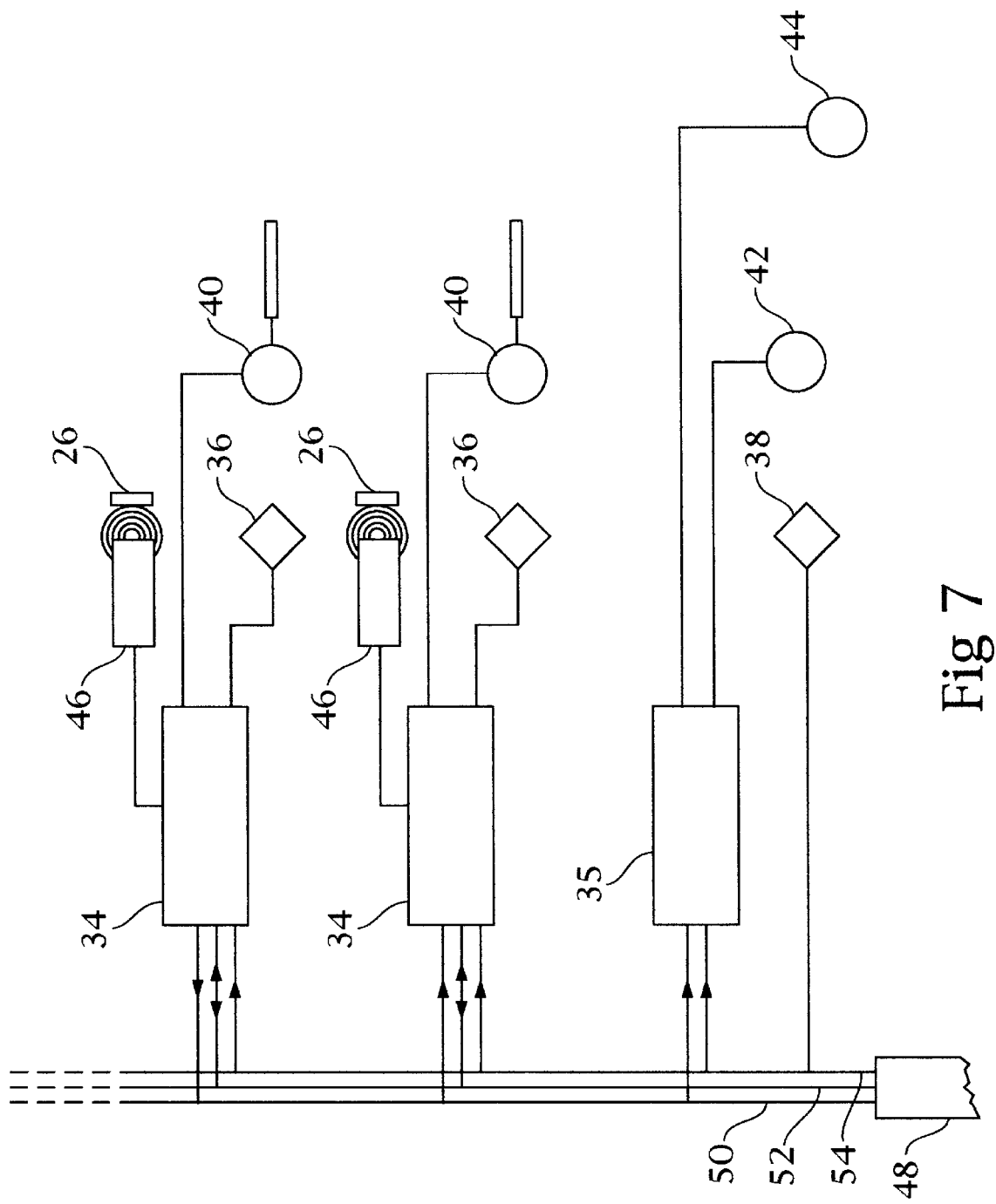
FIG. 7 is a block diagram showing two loading stations in the system using a non-personalized code on the carrier.

The system is composed of the following components (FIG. 7):

1) A module 34 at each loading station 30. A module typically is a micro controller-based PC board.

2) A control unit 35 for the entire system.

3) A sensor 36 at each terminal. The sensor 36 typically is a photo-electric or proximity sensor or a mechanical limit switch.

4) A sensor 38 at the destination station 32. Typically, the sensor 38 is a photo-electric or proximity sensor or mechanical limit switch.

5) Controlled inlet gate 40 at each terminal. Typically the controlled inlet gate is an electric motor or linear actuator.

6) Controlled outlet gate 42 at the destination station. Typically the controlled outlet gate 42 is an electric motor or linear actuator.

7) Vacuum or pressure blower motor 44.

8) Marker 26.

9) Reading device 46 at each inlet station.

10) Communication cable 48 with three lines; execution line 50, lock line 52 and unlock line 54.

When a disposable carrier 10 is properly introduced to the system at a particular loading station 30, the sensor 36 sends a signal to the module 34 indicating that a disposable carrier 10 is at the particular loading station 10. Simultaneously, the reading device 46 at the particular loading station 10 reads the marker 26 on the disposable carrier 10. If the marker 26 matches a code preset in the reading device 46, the reading device 46 sends a confirmation signal to the module 34. The module 34 then:

sends, through line 50, a signal to control unit 35 that controls vacuum/pressure blower motor 44 setting it "on", controls inlet gate 40 of loading station 30 setting it "Open", sends through line 52 a signal to module 34 of all other loading stations blocking the next disposable carrier 10 from being entered into the tube system.

After disposable carrier 10 is accepted into the system, it is propelled by vacuum/pressure through the tube system to closed outlet gate 42 at the destination station 32. The sensor 38 located near the outlet gate 42 discerns a disposable carrier 10 and sends a signal through unlock line 54 to control unit 35. This turns "off" the blower motor 44 and energizes the controlled outlet gate 42 to open the gate. The disposable carrier 10 enters the destination station 32. The signal is also transmitted to each loading station 30 and unlocks all stations to allow a next disposable carrier 10 to be accepted into the system.

Figure 8:
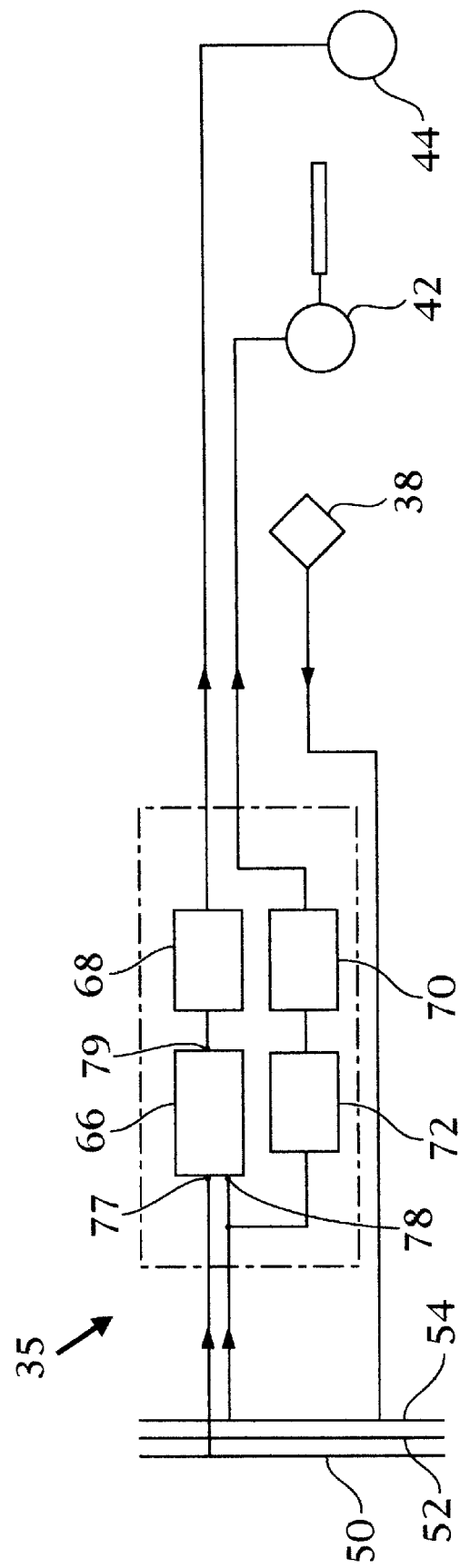
FIG. 8 is a block diagram of the control unit.

The control unit 35 has a control logic module 66, a first control driver 68, a second control driver 70 and a control timer 72 as shown in FIG. 8 The logic module 66 has two inputs 77 and 78 and output 79. An output signal appears only if there is a signal on input 77 and no signal on input 78. Drivers 68 and 70 provide power to the blower motor 44 and the outlet gate 42 respectively. They are based on a power transistor and/or relay. The time delay module 72 works as single-shot timer. When a signal appears on its input, it turns "On" and its output signal lasts for a preset time (long enough for gate 42 to stay open). It is based either on a standard timer or, a simple time delay circuitry integrated with drivers 68 and 70 and logic module 66 on PCB.

When a signal from module 34 is applied through the execution line 50 to input 77 it sets output signal of logic module 66 "On". This signal, amplified by driver 68, sets the blower motor 44 running. The carrier 10, is propelled toward the destination station 32. As sensor 38 sees a carrier 10, near outlet gate 42, it sends a signal through unlock line 54. It sets output signal of logic module "Off", thus disabling motor 44. Simultaneously this signal, through the timer 72 and driver 70, opens the outlet gate 42 allowing the carrier to enter the destination station 32.

Figure 9:
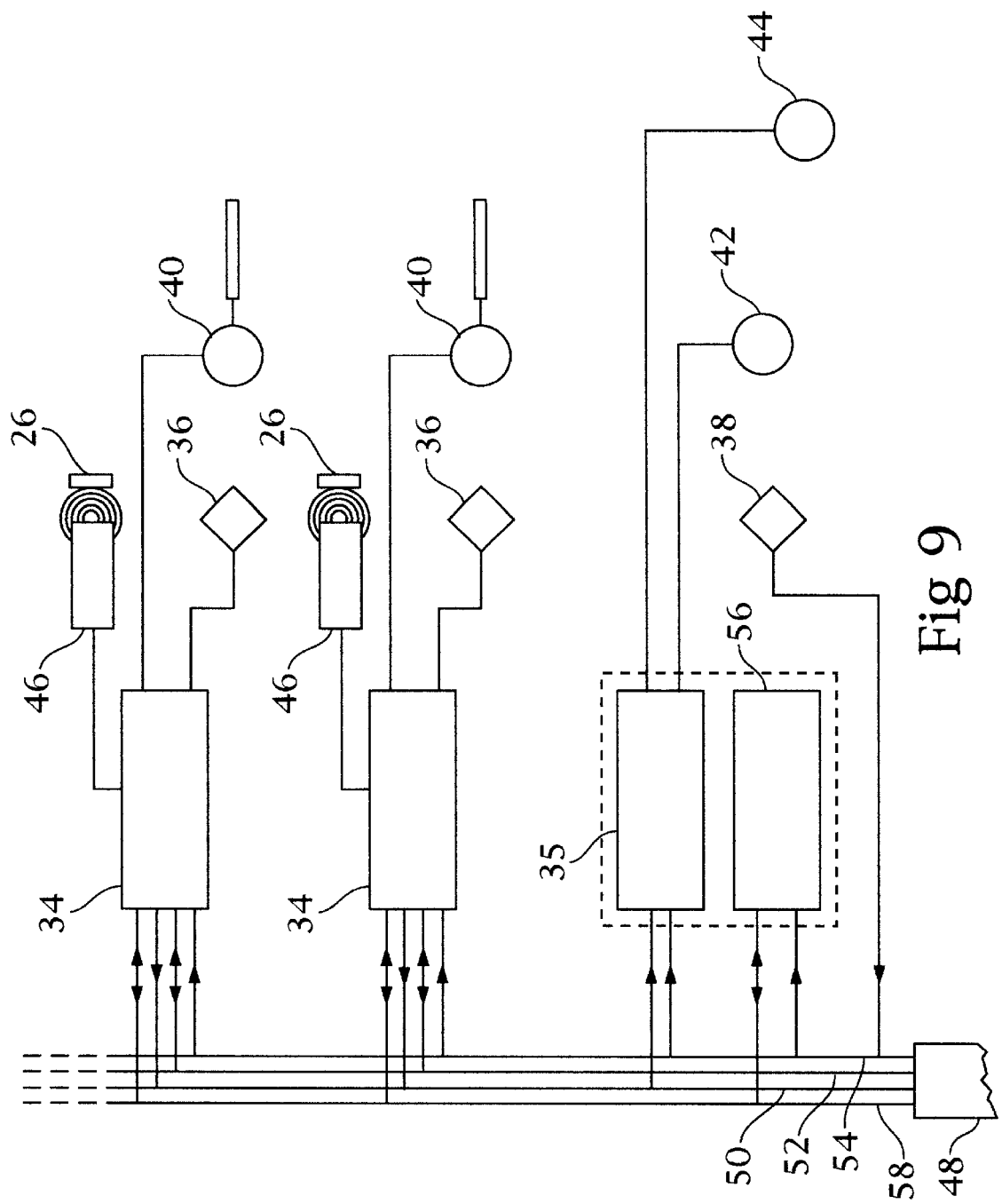
FIG. 9 is a block diagram showing the vacuum system, featuring a carrier with a marker bearing an identification code.
Figure 10:
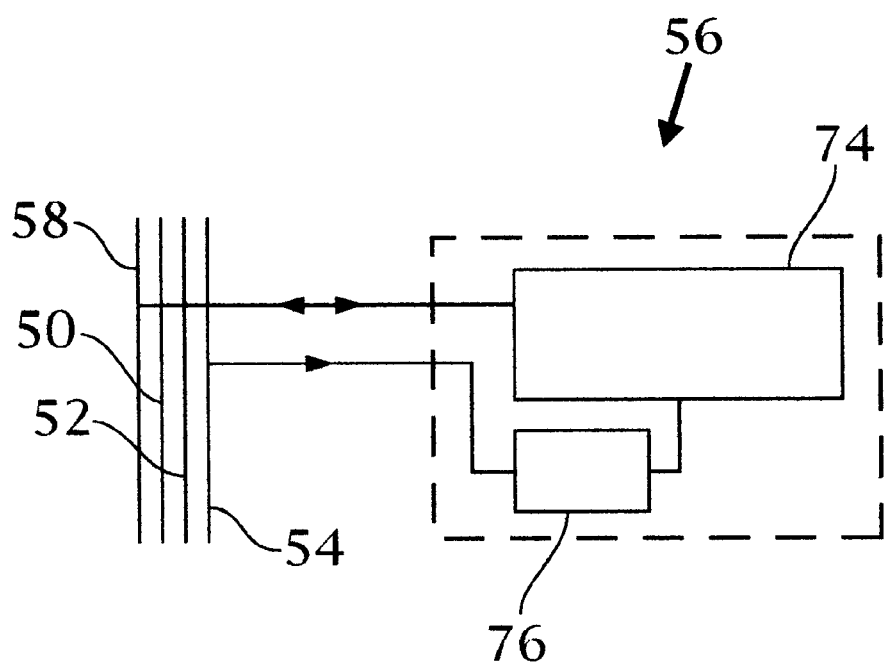
FIG. 10 is a block diagram of the code control unit.

As shown in FIGS. 9 and 10, an additional code control unit 56 and a transmission request data line 58 may be added to the components of the system. Each disposable carrier 10 has a marker 26 providing a unique code. The additional code control unit 56 has the ability to store the legitimate numbers assigned to each disposable carrier 26 in storage 74 and further has the ability to erase numbers which have ben used as carriers are disposed via the delete module 76. In addition to the operation of the system as described above and as shown in FIG. 7, when the reading device 46 reads the identification code of marker 26, it sends the information through the request data line 58 to code control unit 56. In the code control unit 56, the identification code is compared with the legitimate numbers stored therein. If the code matches one of the legitimate stored numbers, the code control unit 56 sends a confirmation signal, through request data line 58, to the module 34 at the particular loading station 30. The system is then activated to deliver the disposable carrier 10 to the destination station 32 as explained above and as shown in FIG. 7. An additional function is performed. When the disposable carrier 10 arrives at the outlet gate 42 at the destination station 32, the signal from the sensor 38 is transmitted to the code control unit 56 as well as to the control unit 35 through the unlock line 54. The code control unit 56 includes the data storage 74 and the erase circuit 76. It is based on a micro controller programmed to be able to communicate with the module 34 through request data line 58. Depending on particular data exchange protocol this line may consist of 1, 2 or more conductors (wires). The code control unit 56 activates an erase circuit and removes the number corresponding to the code on the just received disposable carrier 10. This eliminates the opportunity to send this disposable carrier through the system another time. Also all disposable carriers 10 are accountable. The system discourages theft of "sharps" because the carriers are identified and can be traced as opposed to procedures in use prior to the present invention. The system also prevents misuse of the dedicated pneumatic tube system since only disposable carriers 10 with the appropriate marker can activate the control unit 35.

The disposal carrier 10 with its marker 26 and the control unit 35 operate the system. The only interface with an operator is for the operator to place the sharps in the container 14, place the cover 20 on the container 14 and introduce the disposable carrier 10 into the loading station 30. The operator does not select the destination of the disposable carrier 10 and does not separately activate the pneumatic tube system. There is no control panel for the operator to use. The operator cannot 15 stop the movement of the disposable carrier 10 through the pneumatic tube system nor can the operator send anything except the disposable carrier 10 through the pneumatic tube system.

The control unit 35 regulates and controls the movement of the disposable carrier 10 through the pneumatic tubes such that only one disposable carrier 10 may move through the system at a given time. While one disposable carrier 10 is being transported from a given loading station 30 to the destination station 32, no other disposable carrier may be transported simultaneously in the pneumatic tubes. p The present invention provides a safe, secure uncontaminated environment in which to move "sharps" from loading stations or various separated locations to a single destination station with a minimum of operator input.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. The method of disposing of biohazardous and/or hazardous "sharps" in a healthcare, hospital or clinical environment, comprising the steps of providing a dedicated single-purpose pneumatic tube system having a plurality of loading stations and a single destination station, providing a plurality of disposable carriers, each carrier having an identification means, providing a pneumatic tube system control unit activated by the identification means on each of the disposable carriers, wherein an operator inserts "sharps" in a selected one of the disposable carriers, seals said disposable carrier and introduces said disposable carrier into the pneumatic tube system at any loading station, and the pneumatic tube system transporting the disposable carrier containing the sharps to the destination station without any operator action.

2. The method of claim 1, wherein the system control unit controls movement of disposable carriers such that only one disposable carrier may move through the pneumatic tube system at a given time.

3. The method of claim 1, further comprising providing an individual identification code to each disposable carrier, providing a code control unit electronically connected to the pneumatic tube system, wherein the code control unit stores the code of each of the disposable carriers.

4. The method of claim 3, wherein the code control unit identifies each disposable carrier introduced into the system an activates the pneumatic tube system.

5. The method of claim 4, further comprising a placing sensor at the destination station, the sensor providing a signal to the code control unit, the signal activating an erase circuit and deleting the individual code of the respective disposable carrier, thereby preventing reuse of the respective disposal carrier and accounting for all of the disposable carriers.

6. The method of disposing of biohazardous and/or hazardous "sharps" in a healthcare, hospital or clinical environment, comprising the steps of providing a dedicated single-purpose pneumatic tube system having a plurality of loading stations and a single destination station, providing a plurality of disposable carriers, each carrier having an individual identification code, providing a pneumatic tube system control unit, providing a code control unit electronically connected to the pneumatic tube system, inserting sharps in the disposable carrier, placing the disposable carrier containing the sharps in one of the loading stations, the code control unit recognizing the individual identification code on each disposable carrier and the code control unit activating the pneumatic tube system, the pneumatic tube system transporting the disposable carrier containing the sharps to the destination station without any operator action.

7. The method of claim 6, wherein the code control unit controls movement of disposable carriers such that only one disposable carrier may move through the pneumatic tube system at a given time.

8. The method of claim 6, further comprising placing a sensor at the destination station, the sensor providing a signal to the code control unit, the signal activating an erase circuit and deleting the individual code of the respective disposable carrier, thereby preventing reuse of the respective disposal carrier and accounting for all of the disposable carriers.

* * * * *